US 6,575,973 B1

(12) United States Patent
Shekalim

(10) Patent No.: US 6,575,973 B1
(45) Date of Patent: Jun. 10, 2003

(54) SELF LOCKING INTRAMEDULLARY NAIL

(75) Inventor: Avraham Shekalim, Nesher (IL)

(73) Assignee: Safedrip Ltd., Migdaz Haemek (IL)

( * ) Notice: Subject to any disclaimer, the term of this patent is extended or adjusted under 35 U.S.C. 154(b) by 65 days.

(21) Appl. No.: 09/696,234

(22) Filed: Oct. 26, 2000

(51) Int. Cl.$^7$ ................................................. A61F 5/04
(52) U.S. Cl. ............................................ 606/62; 606/68
(58) Field of Search ....................... 606/62, 63, 66–68; 411/21, 24

(56) References Cited

U.S. PATENT DOCUMENTS

| | | | |
|---|---|---|---|
| 3,986,504 A | * 10/1976 | Avila | |
| 4,237,875 A | * 12/1980 | Termanini | |
| 4,262,665 A | * 4/1981 | Roalstad et al. | |
| 4,275,717 A | * 6/1981 | Bolesky | |
| 5,057,103 A | * 10/1991 | Davis | 606/63 |
| 5,268,000 A | * 12/1993 | Ottieri et al. | 606/62 |
| 5,534,004 A | * 7/1996 | Saniangelo | 606/68 |
| 5,645,589 A | * 7/1997 | Li | 623/16 |
| 5,702,215 A | * 12/1997 | Li | 411/21 |
| 5,843,127 A | * 12/1998 | Li | 606/232 |
| 6,022,373 A | * 2/2000 | Li | 606/232 |
| 6,129,762 A | * 10/2000 | Li | 623/13.11 |
| 6,149,669 A | * 11/2000 | Li | 606/232 |

* cited by examiner

Primary Examiner—Ralph A. Lewis
(74) Attorney, Agent, or Firm—G.E. Ehrlich Ltd.

(57) ABSTRACT

An internal fixation device particularly useful for securing bone fragments which includes an elongate tubular sleeve for insertion into the medullary canal of the bone fragments to be secured; an elongate shaft movable within the sleeve; and at least two anchoring elements, each having an inner end coupled to the shaft and an outer end aligned with a slot in the sleeve and displaceable radially outwardly therethrough to engage a bone fragment upon the movement of the shaft within the sleeve. The inner ends of the anchoring elements coupled to the shaft are oriented such that the outward displacement of one anchoring element anchors the engaged bone fragment against movement in one longitudinal direction, and the outward displacement of the other anchoring element anchors the engaged bone fragment against movement in the opposite longitudinal direction.

20 Claims, 5 Drawing Sheets

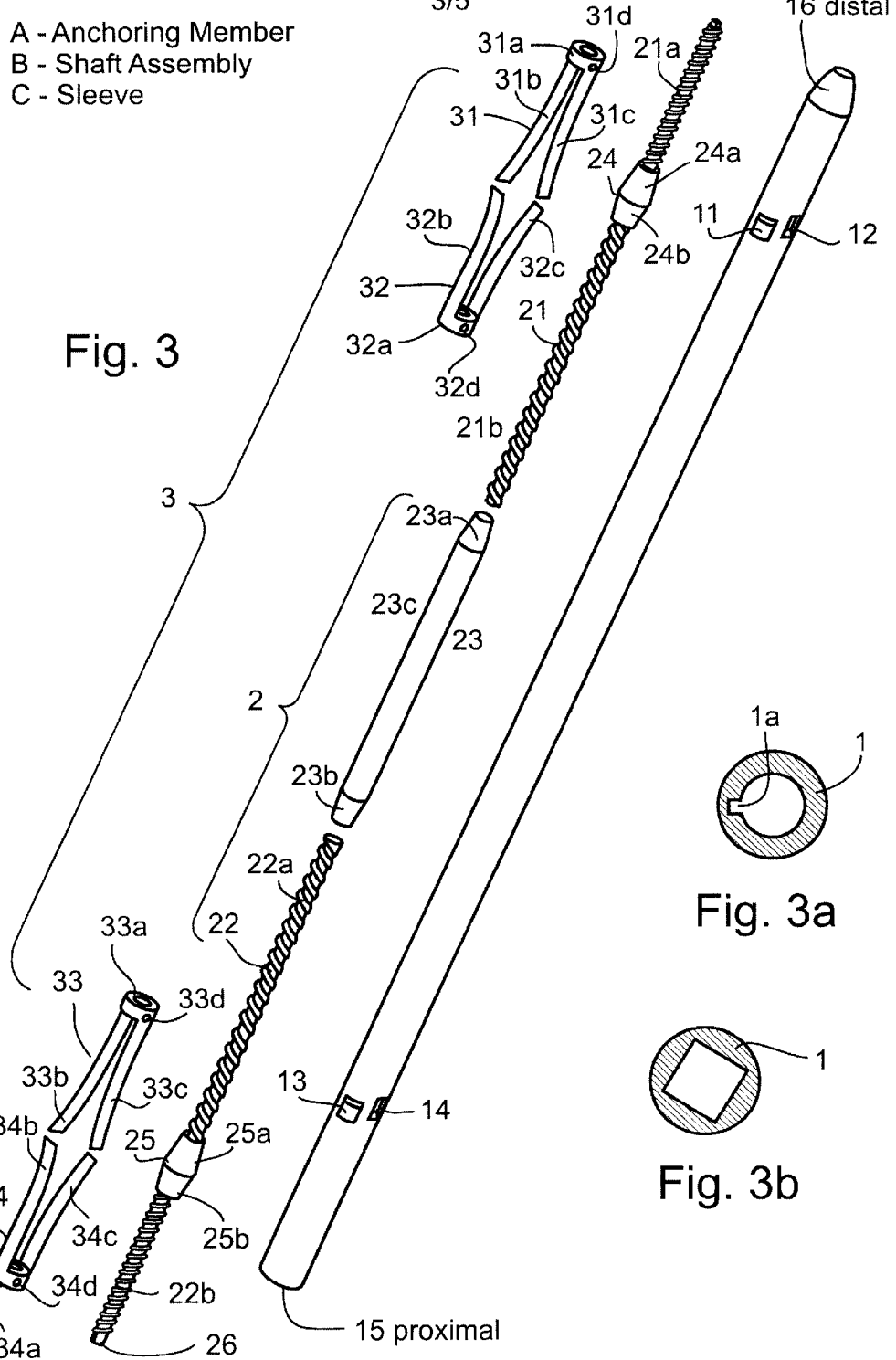

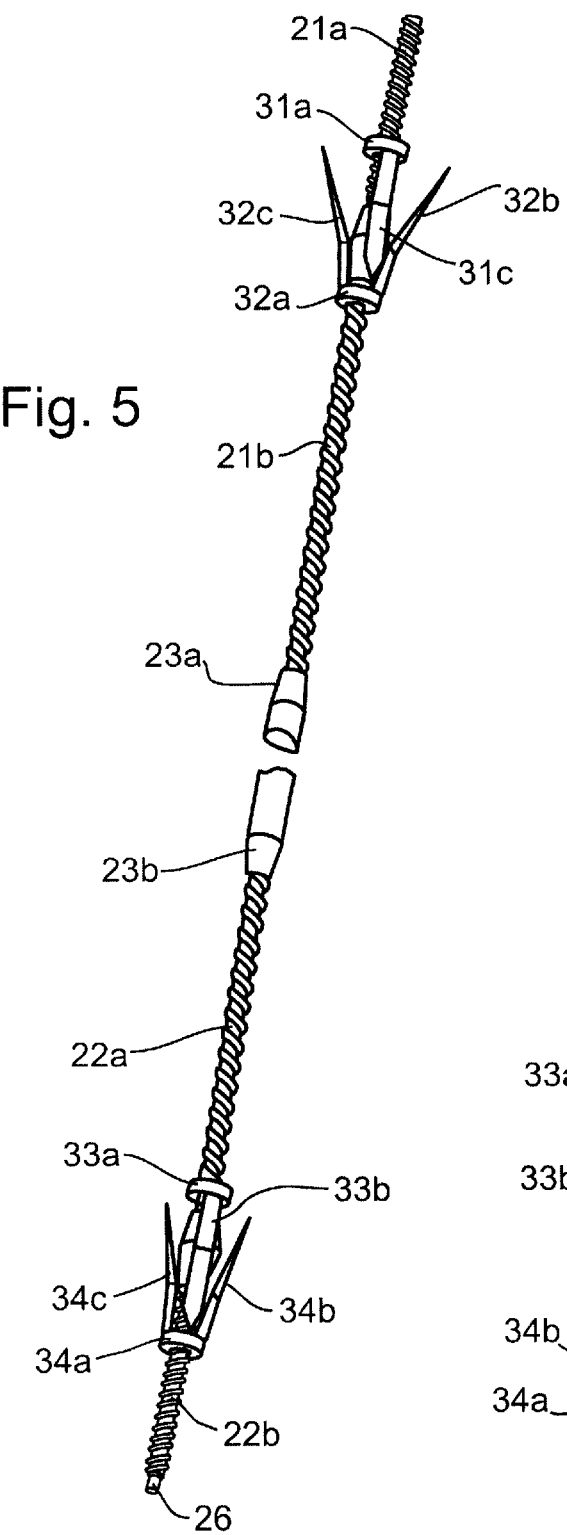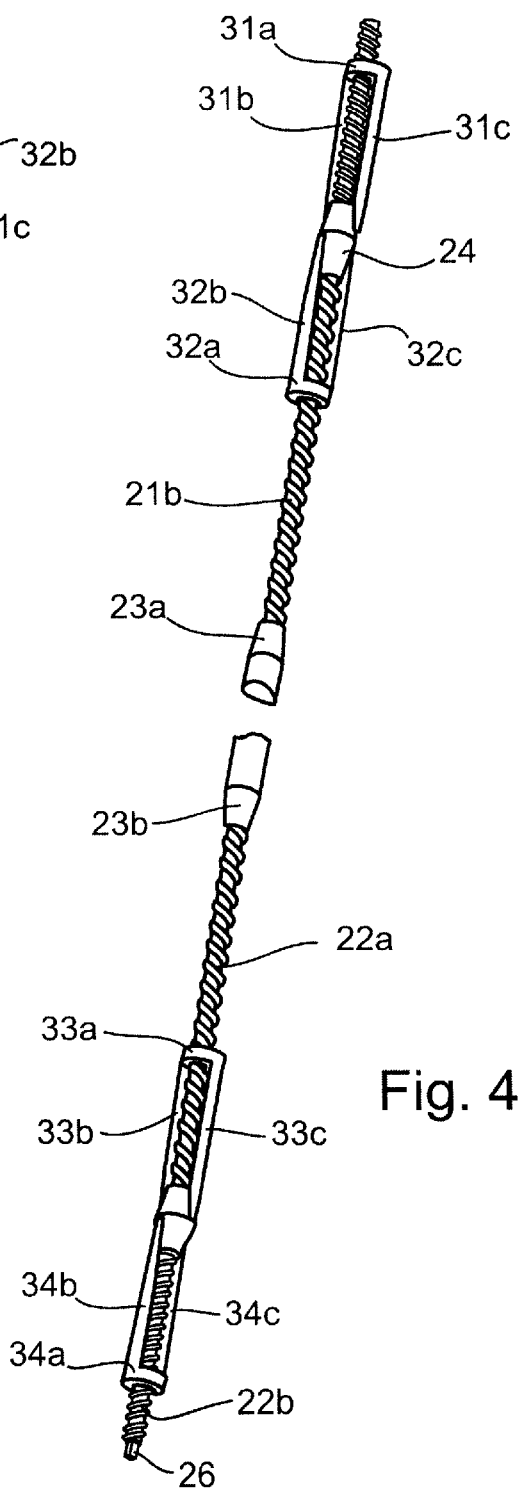
Fig. 5
Fig. 4

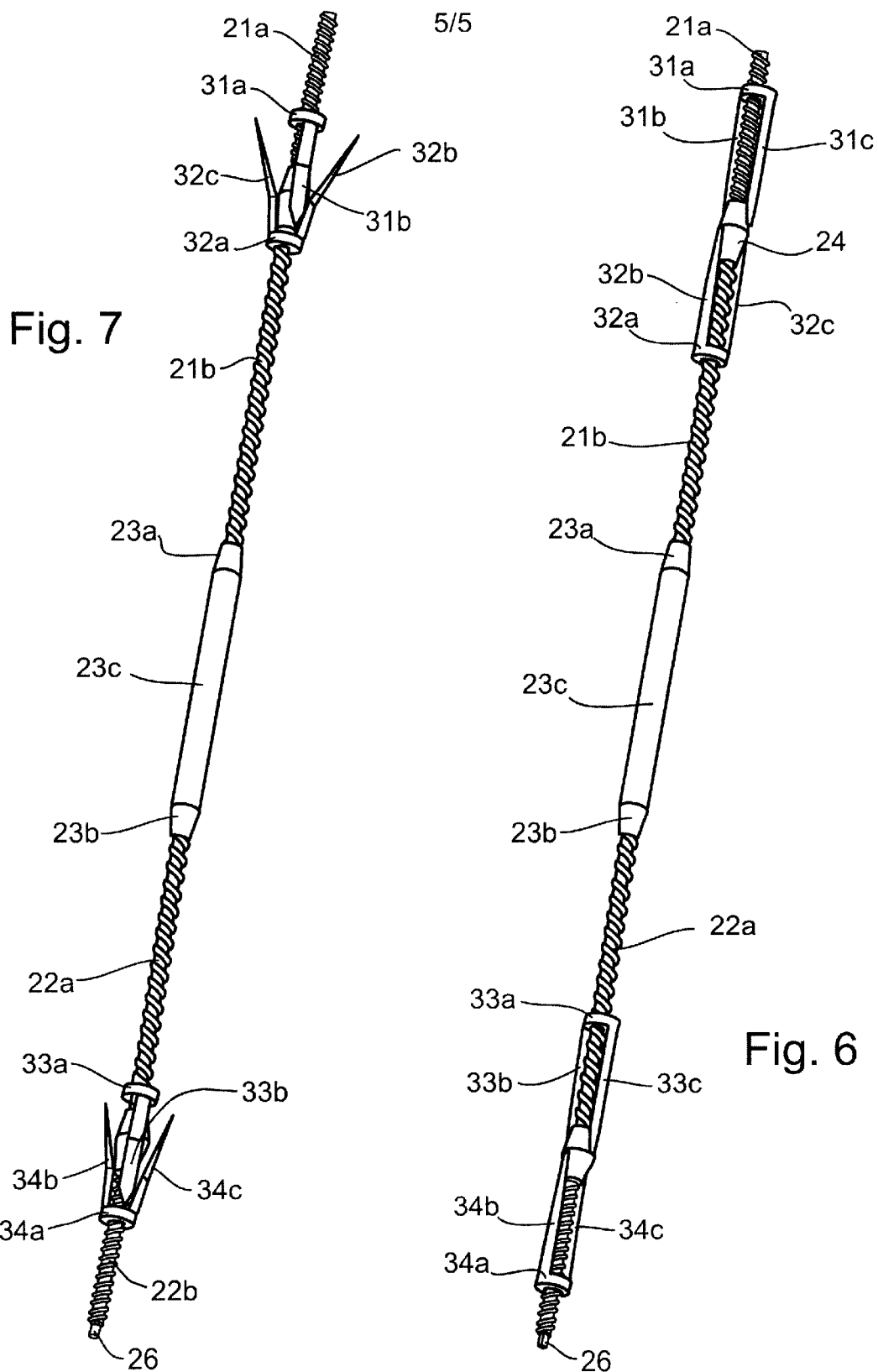

SELF LOCKING INTRAMEDULLARY NAIL

FIELD OF INVENTION

The invention relates to surgical devices for fixing broken bones and in particular to an improved intramedullary fixation device for securing broken bone fragments during the process of fracture healing.

BACKGROUND

Bone fractures are treated by realigning the broken bone fragments and immobilizing them in their formerly healthy positions relative to one another until the body causes the bone to heal and restore its structural integrity. Immobilization or fixation of the segments is accomplished by the use of rigid devices that span the fracture site and are located either external to the body or internally on the bone surface or inside the medullary canal.

Intramedullary fixation devices, which are indicated primarily in the fracture of long tubular bones, offer substantial advantages over external devices or those that are attached to the external surface of the bone. Such advantages include restoring functional rehabilitation of the limb within a relatively short time, freedom from the need for multiple surgical incisions to insert and remove holding pins and screws, reduced fluoroscopy, reduced incidence of infection and, unlike external holding devices, they are not easily susceptible to inadvertent movement.

Although intramedullary nailing has been used for many years, the devices presently in use are not completely satisfactory. Prior art reflects a multiplicity of devices, each with different characteristics:

The Kuntschner nail, developed in Germany in the 1930s, relies upon a cloverleaf cross-section, coupled with the lateral resilience afforded by a longitudinal slot, to maintain a stationary position within the medullary canal. It offers no other holding means to anchor it to the osseous wall of the canal. While this may be somewhat effective in holding the proximal bone fragment due to the relatively large area of surface contact, it is not reliable in holding the distal fragment, particularly when the fracture is located well into the distal portion of the bone where the medullary canal widens in cross-section. Attempts have been made to solve this problem by designing intramedullary nails which abandon the clover leaf cross-section design and instead rely upon expanding mechanisms within the nail to gain purchase on the osseous wall of the medullary canal within the distal bone fragment. None does so effectively.

U.S. Pat. No. 4,453,539, granted to Raftopoulos, et al, discloses a nail having a uniform circular cross-section and elements which extend radially out the sides of the distal portion, effectively increasing the diameter of the shaft near its distal end. While this device is capable of making contact with the inside of the medullary canal, because of the shape and orientation of the extending elements, it is not capable of attaining a good grip on it. Moreover, the extending elements engage only the distal bone fragment and do not engage the proximal fragment. Therefore, this nail provides only limited lateral support and allows potential rotational and migratory movement of the bone fragments relative to one another.

The problem with this nail and the other examples of the prior art is their inability to get a good purchase on the osseous wall of the medullary canal. Typically, the longitudinally extending medullary canal within a tubular bone has an irregular contour that generally converges in the central portion of the bone and diverges in a longitudinal direction near the ends of the bone. Consequently, an intramedullary nail that merely extends elements radially to make contact with the osseous wall will not secure a good grip, particularly when the bone is subjected to the substantial forces of functional rehabilitation, such as walking, prior to its healing. Moreover, an intramedullary nail having a uniform circular cross-section with no gripping means at its proximal end will only contact the inner wall of the medullary canal over a small region. Without a gripping method within both the proximal and the distal fragment, such a nail fails to provide sufficient lateral support to the fractured bone.

The intramedullary device disclosed by Wills, et al, in U.S. Pat. No. 4,519,100, similarly has a circular cross section and employs an expanding mechanism to grip the distal fragment of the bone. The device employs pivotal blades which rotate outwardly to engage the distal end of the fractured bone, resting in a flared configuration at the distal end of the medullary canal. Accordingly, these blades do not provide a positive force opposing movement of the distal fragment in the distal direction, particularly as their proximal edges are sharp and may allow movement as they easily penetrate the osseous wall. Moreover, this device does not securely engage the proximal fragment. Therefore, it too suffers the same deficiencies in providing lateral support. Indeed, the Wills patent acknowledges the deficiency by suggesting the insertion of a screw through the proximal bone fragment wall into the device in order to afford fixation.

Kurth U.S. Pat. No. 4,590,930 deploys an expanding device at the distal end of a cloverleaf cross-section nail. This device has three drawbacks. The first is that the mechanism employed for extending and retracting the blades is unduly complicated and relies on close tolerances in order to function within the clover leaf cross-section. The second is that the extending blades are necessarily of a very short length and may not reach or securely attach to the canal wall. The third is that it continues to rely upon the cloverleaf shape to grip the proximal fragment. While superior to a circular cross-section, this method is far less effective than an expansion device that securely engages the osseous wall within the medullary canal.

Prior art discloses other fixation devices that attempt to address the dual objectives of attaining secure anchoring into the bone fragment and securely gripping both the proximal and distal bone fragments in a manner that does not cause compression of the fragments. However, none of them satisfactorily achieves either of these goals. There exists no intramedullary device that employs a holding means that grips the bone fragment in both longitudinal directions so that it can withstand the forces caused by functional rehabilitation prior the complete healing of the bone. Moreover, all of those devices that have a holding means in both the proximal and distal fragments exert compressive force on the fragments in order to achieve anchoring. This is not always indicated nor desirable after reduction of the fracture, particularly in the case of comminuted fractures.

U.S. Pat. No. 4,091,806 to Aginsky shows a device that secures the distal fragment by means of a distally located expanding mechanism that consists of a conical member, which rides on a longitudinally disposed threaded rod, which spreads the split distal end of the nail apart when the rod is rotated. This method grips poorly because the split portion of the nail making contact with the inside of the medullary canal in the distal fragment is of circular shape which is not able to penetrate for holding securely to the osseous wall. Substantial pressure against the wall of the fragment is needed which holds the potential for additional damage to the bone. Moreover, this device exerts considerable compression on the fragments because the force opposing the movement of the conical member longitudinally along the shaft is a nut embedded in the proximal end of the proximal fragment. This design has additional drawbacks. One or more of the split ends can break off when extended by the conical member. When it is necessary to remove the nail after the bone is healed, this design relies solely on the restorative resiliency of the split nail ends to contract the expanded portion of the nail; a small piece of bone fragment or marrow growth lodging between the threaded rod and one or more of the split nail ends could frustrate the nail removal process.

U.S. Pat. No. 4,275,717 to Bolesky is another example of a device which engages both the proximal and distal fragments, but does so by causing compression of the fragments. This nail has a circular plurality of gripper fingers extending radially that engage the medullary canal wall of the distal fragment in one longitudinal direction only. There is no actuating means which directly causes the extension of the fingers. Anchoring is achieved within the distal fragment solely by being pulled toward the proximal fragment, causing compression of the fragments. Indeed, the effectiveness of the anchoring is directly proportional to the compressive force applied, which holds substantial potential for additional damage to the bone.

Another attempt is disclosed by Avila, in U.S. Pat. No. 3,986,504, which is an intramedullary device which has a set of radially extending fins arrayed axially in both the proximal and distal fragments of the bone. However, each set of fins is oriented in one longitudinal direction only and engages the medullary canal wall within its respective fragment as the two sets are simultaneously being pulled toward one another, exerting compressive force on the fragments.

Davis, in U.S. Pat. No. 5,057,103, shows an intramedullary fixing device which has hook like arms at its distal end that extend to engage the canal wall in the distal fragment by pulling the distal fragment toward the proximal fragment. These hooks are oriented to engage only by so pulling the fragments together and causing compression of the fracture.

In U.S. Pat. No. 4,237,875, Termanini has designed a device which has protruding spikes in both the proximal and distal fragments. However, the spikes are very short because the design of the actuating means necessarily limits their length to that which can be retracted radially into the shaft of the device. Accordingly, it may not gain a secure purchase on the intramedullary canal wall. Moreover, the actuating means is excessively complex, relying on members that slide within one another with very close tolerances. In addition, this device is specifically designed to exert compressive force on the bone fragments.

What is needed is an intramedullary fixing device that securely anchors to a bone fragment and is capable of holding both fragments of a broken bone in place without exerting compressive force upon them.

SUMMARY OF THE INVENTION

An object of the present invention is to provide a novel anchoring mechanism within an intramedullary fixing device which has a number of important advantages over the existing devices as will be described more particularly below.

According to a broad aspect of the present invention, there is provided an internal fixation device particularly useful for securing bone fragments, comprising an elongated tubular sleeve which has at least two slots therethrough designed for insertion into the medullary canal of a bone; an elongate shaft assembly disposed longitudinally and coaxially within the sleeve; and at least two anchoring elements having their inner ends coupled to the shaft assembly and their outer ends aligned with the slots in the sleeve, which may be extended radially outwardly through the slots to engage the bone fragment. The inner ends of the anchoring elements are coupled to the shaft and are oriented obliquely in opposite longitudinal directions such that the outward extension of one anchoring element anchors the bone fragment against movement in one longitudinal direction and the outward extension of the other anchoring element anchors the bone fragment against movement in the opposite longitudinal direction. The outer end of each of the anchoring elements is shaped so as to securely engage the osseous layer of the medullary canal within the bone fragment.

According to further features in the preferred embodiment of the invention described below, the outer ends of the anchoring elements are pointed so as to penetrate the engaged home fragment when the outer end is displaced radially outwardly. Such anchoring elements are therefore frequently fermed "spikes" in the description below.

According to further features in the described preferred embodiment, the shaft assembly is rotatably moveable with respect to the sleeve. The inner ends of the anchoring elements are coupled to the shaft by means of nuts threaded on the shaft. The spikes protrude longitudinally from the nuts. More than one spike may protrude from each of the nuts. All spikes protruding from the same nut are oriented in the same longitudinal direction and are arrayed equidistantly at the circumference of the nut. The nuts are disposed upon the shaft assembly such that two nuts comprise a set, with the nuts comprising a set being located proximal to one another and oriented such that the spikes protruding from one nut extend in the opposite longitudinal direction from the spikes protruding from the other nut within the set. The spikes protruding from the two nuts within the set are arrayed alternatively and are offset equidistantly.

The shaft assembly includes at least one segment of right hand threads and at least one segment of left hand threads, on each of which is disposed one of the nuts comprising a set. The shaft is rotatable relative to the nuts. The two nuts are oriented such that by rotating the shaft clockwise, the two move toward each other and by rotating the shaft counterclockwise the nuts move away from each other. The nuts are oriented within the sleeve such that the spikes protruding therefrom are displaced through the slots upon the movement of the nuts.

A cam member in the shape of a cylindrical double ended cone which diminishes in diameter in both directions from its center is fixed coaxially on the shaft assembly equidistantly between the nuts and is oriented with respect to the slots such that the cam surface deflects the spikes radially outwardly through the slots.

The proximal end of the shaft assembly is configured to accept a torqueing device. Clockwise rotation of the shaft causes the spikes to extend through the slots to engage the bone fragment. Counterclockwise rotation of the shaft causes the spikes to disengage from the bone fragment and retract within their respective slots. The spikes are adapted to be fully retracted within the sleeve, leaving a smooth cylindrical surface for easy insertion and withdrawal.

According to other aspects of the invention, the device is variable both in length and diameter and is adaptable to array more or less spikes, with differing dimensions and configurations, as may be appropriate under specific circumstances. The device may be cannulated or non cannulated, as needed. All parts of the device are made of noncorrosive biologically compatible materials.

An important feature in the described preferred embodiment of the invention lies in the anchoring mechanism it employs to engage the osseous wall within the medullary canal. This mechanism, which includes a plurality of anchoring elements alternatively oriented in the proximal and distal directions, engages the osseous wall in both longitudinal directions simultaneously, causing a gridlock effect with each spike preventing the disengagement or movement of the adjacent spike. This feature has three important advantages: first, by anchoring in both longitudinal directions simultaneously, it prevents any movement that might be caused by the deployment of the device itself; second, the forces that the device exerts upon the bone fragment are balanced in all directions such that the engagement and disengagement of the spikes does not cause additional damage to the bone; and third, its configuration allows the employment of spikes of varying lengths which can accommodate any size medullary canal.

Another important feature lies in providing an anchoring mechanism at both the proximal and the distal ends of the device which holds both the distal and proximal fragments of the broken bone securely in place without causing compression of the bone fragments. There presently exists no intramedullary nail which does this without externally applied fixing devices such as screws or pins to anchor the nail to the bone fragments. The present invention accomplishes this effectively without external means.

Accordingly, the device disclosed herein offers many advantages over the existing intramedullary fixing devices: It securely anchors to either or both of the fragments of a broken bone in a manner that does not cause further damage to the bone; it secures both the proximal and the distal bone fragments with great lateral stability in a manner that does not cause compression of the fragments; it effectively prevents rotational, angular, shearing and migratory movements of the bone fragments during the healing process; it has a holding mechanism sufficiently versatile to accommodate medullary canals of different internal dimensions and configurations; it is easily inserted and removed without excessive surgery or fluoroscopy; it can be engaged and disengaged simply and in a controlled manner; it may be cannulated or non-cannulated as needed; it is simple, rugged and reliable in design and is inexpensive to manufacture.

BRIEF DESCRIPTION OF DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 3 is an exploded view of the nail of FIG. 1;

FIG. 3a is a sectional view along line a—a of FIG. 3;

FIG. 3b is a corresponding view illustrating a modification;

FIG. 4 is a perspective view of the partially assembled nail of FIG. 1 with the anchoring elements in their retracted inoperative position;

FIG. 5 is a view similar to that of FIG. 4 but showing the anchoring elements in their extended operative position;

FIG. 6 is a perspective view of the fully assembled internal mechanism of the nail of FIG. 1 with the anchoring elements in their retracted inoperative position; and FIG. 7 is a view similar to that of FIG. 6 but showing the anchoring elements in their extended operative position.

GENERAL DESCRIPTION OF PREFERRED EMBODIMENT

Figure 1:
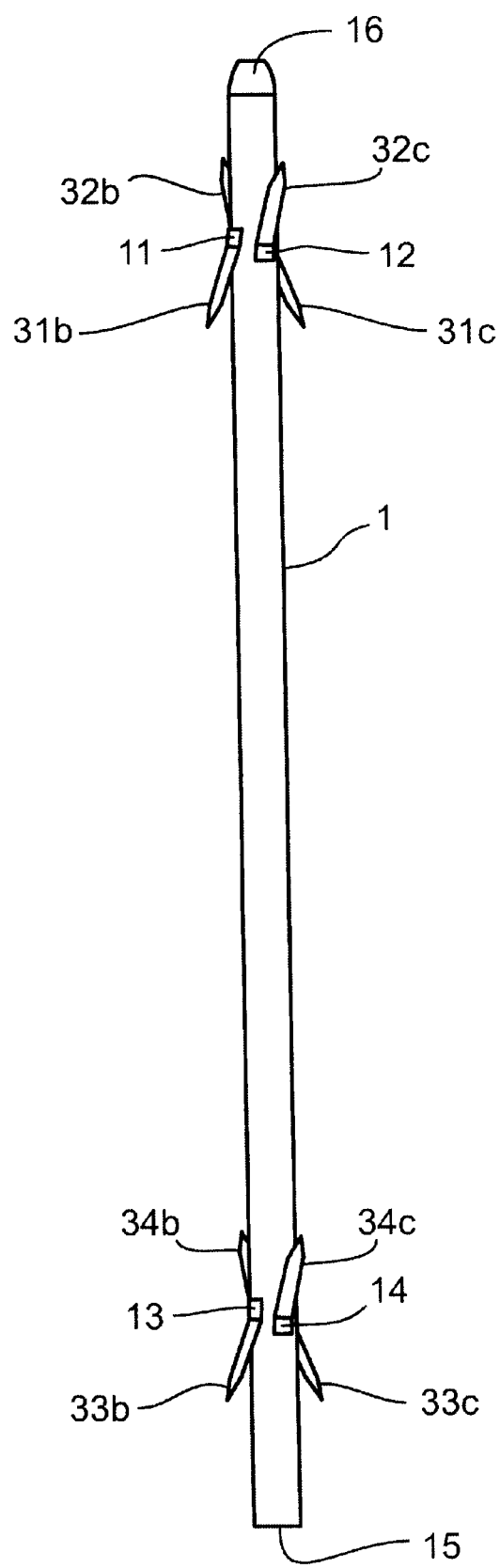
FIG. 1 is a longitudinal view of a self-locking intramedullary nail constructed in accordance with the invention, configured with an anchoring member comprising two sets of four anchoring elements, each in an extended operative position.
Figure 2:
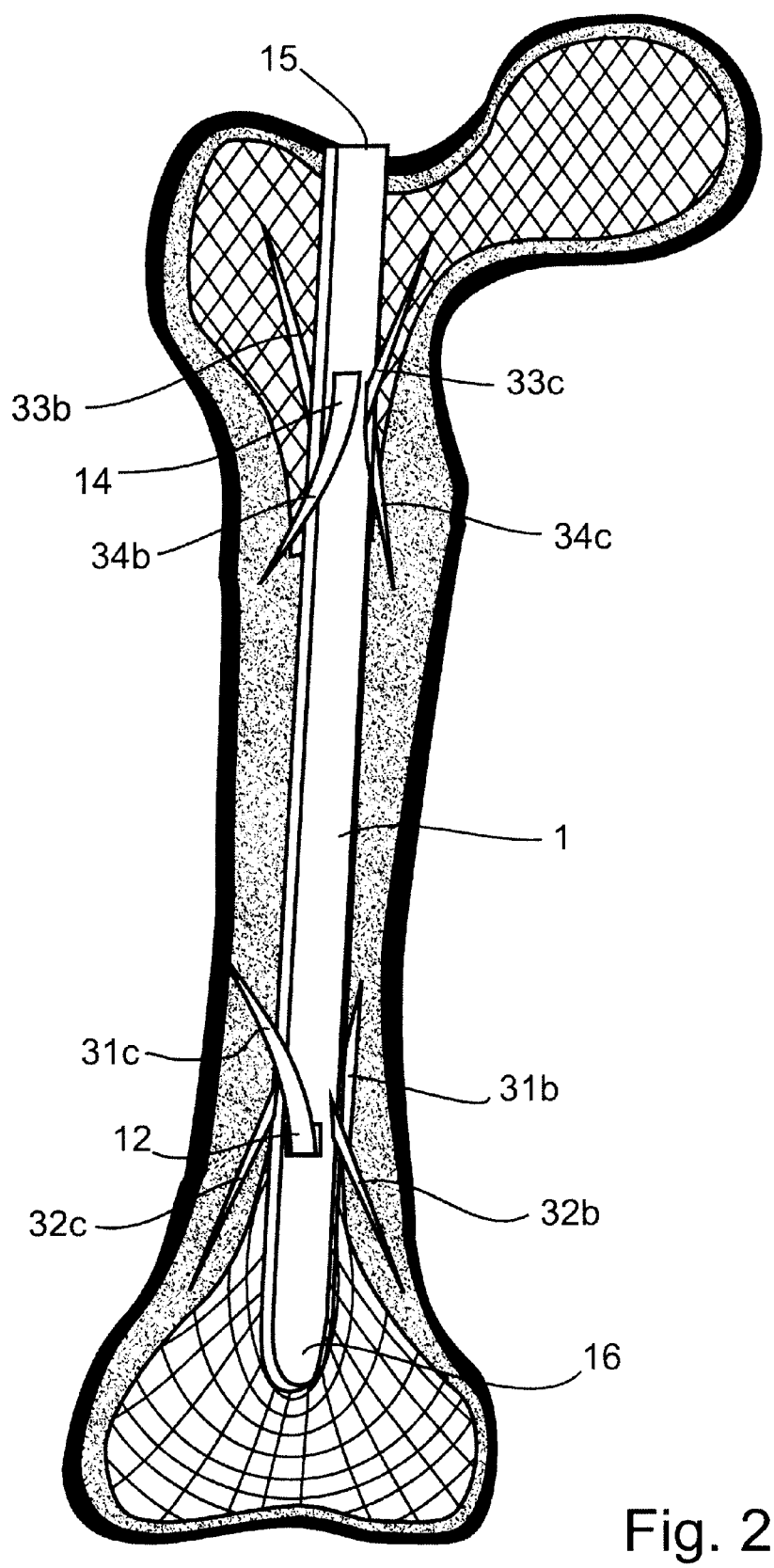
FIG. 2 is an illustration of the nail of FIG. 1 deployed within a femur.

The self locking intramedullary nail illustrated in the drawings comprises three main components or assemblies: a sleeve 1, a shaft assembly 2, and a plurality of anchoring members generally designated 3.

As shown particularly in FIG. 3, the illustrated nail includes four anchoring members to define two sets of four anchoring elements. One set is constituted of the two anchoring members 31, 32 having anchoring elements 31b, 31c, 32b, 32c, and is disposed near the distal end; and one set is constituted of the two anchoring members 33, 34 having anchoring elements 33b, 33c, 34b, 34c, and is disposed near the proximal end.

The elongate tubular sleeve 1 has a distal end 16 which is adapted to be inserted within the medullary canal of a bone and a proximal end 15 of which is open. The sleeve 1 has a set of four circumferentially and equidistantly arrayed slots 11–12 close to its distal end 16 and a set of four circumferentially and equidistantly arrayed slots 13–14 close to its proximal end 15.

Also depicted is an elongate shaft assembly 2 comprising a threaded rod at its distal end 21 and a threaded rod at its proximal end 22. The threaded rod at the distal end 21 includes a segment of right-hand threads 21a and an adjacent segment of left-hand threads 21b. At the juncture of the two segments is disposed a double ended conical cam member 24 which diminishes in diameter in both directions from its center. The threaded rod at the proximal end 22 includes a segment of right-hand threads 22a and an adjacent segment of left-hand threads 22b. At the juncture of the two segments is disposed a double ended conical cam member 25 which diminishes in diameter in both directions from its center. The two threaded rods 21 and 22 are joined together by a coupling member 23 which is affixed to the distal end of the proximal rod 22 by means of end cap 23a and affixed to the proximal end of the distal threaded rod 21 by means of end cap 23b. The end caps 23a and 23b join with central coupling tube 23c such that they are not relatively rotatable. FIGS. 4 and 5 show the shape of end caps 23a and 23b. The two end caps 23a and 23b, when joined with central coupling tube 23c, form one coaxial shaft assembly from the two threaded rods, all parts of which rotate together.

As shown in FIG. 3, the anchoring is effected by two sets of two interlocking anchoring members 31–32 and 33-34.

Set 31–32 includes: a distal anchoring member 31 which comprises a nut 31a and two anchoring elements or spikes 31b, 31c; and a proximal anchoring member 32 which comprises a nut 32a and two anchoring elements or spikes 32b, 32c. The inner ends of spikes 31b and 31c are attached to nut 31a. The outer ends of spikes 31b and 31c protrude from nut 31a longitudinally in the proximal direction, arrayed equidistantly at the circumference of nut 31a. The inner ends of spikes 32b and 32c are attached to nut 32a. The outer ends of spikes 32b and 32c protrude from nut 32a longitudinally in the distal direction, arrayed equidistantly at the circumference of nut 32a. Set 33–34 includes a distal anchoring member 33 which comprises a nut 33a and two spikes 33b and 33c and a proximal anchoring member 34 which comprises a nut 34a and two spikes 34b and 34c. The inner ends of spikes 33b and 33c are attached to nut 33a. The outer ends of spikes 33b and 33c protrude from nut 33a longitudinally in the proximal direction arrayed equidistantly at the circumference of nut 33a. The inner ends of spikes 34b and 34c are attached to nut 34a. The outer ends of spikes 34b and 34c protrude from nut 34a longitudinally in the distal direction arrayed equidistantly at the circumference of nut 34a.

Preferably, each of the anchoring members 31–34 is integrally formed with its nut and anchoring elements, and is made of an elastic material (e.g., spring steel) such that the outward displacement of the anchoring elements is effected by elastic deformation via the cam members 24, 25 as described below.

The shaft assembly is fully assembled and configured as shown in FIG. 6 prior to insertion. Anchoring members 31–32 are threadably mounted on distal threaded rod 21 such that nut 31a engages the segment of right-hand threads 21a with spikes 31b and 31c oriented proximally, and nut 32a engages the segment of left-hand threads 21b with spikes 32b and 32c oriented distally. Anchoring elements 33–34 are threadably mounted on proximal threaded rod 22 such that nut 33a engages the segment of right-hand threads 22a with spikes 33b and 33c oriented proximally and nut 34a engages the segment of left-hand threads 22b with spikes 34b and 34c oriented distally. Each set of anchoring members 31–32 and 33–34 is disposed upon the shaft assembly 2 such that the spikes protruding from its distal element and the spikes protruding from its proximal element are alternatively arrayed circumferentially and equidistantly, forming an interlocking pattern of spikes.

The shaft assembly 2, with the anchoring members 31–34 disposed thereon, is mounted longitudinally and coaxially for rotational movement within the sleeve.

The shaft assembly 2, with the anchoring members 31–34 disposed thereon, is mounted longitudinally and coaxially for rotational movement within the sleeve 1. The shaft assembly 2 is fitted into the sleeve 1 oriented such that the cam members 24 and 25 are longitudinally disposed opposite their respective sets of slots and with all of the spikes circumferentially and longitudinally aligned adjacent to their respective slots.

The device is inserted into the bone surgically in the customary manner with the anchoring members 31–34 in their retracted inoperative positions. In order to affix the device within the bone, the spikes are extended through their respective slots in the sleeve 1 until they engage the osseous wall of the medullary canal.

The spikes are displaced through the slots by means of the rotation of the shaft assembly 2, the proximal end 26 of which is configured to accept a torqueing means (not shown). The shaft assembly 2 is rotatable relative to the anchoring members 31–34. During the shaft rotation each anchoring member moves longitudinally but remains fixed in its circumferential orientation relative to the sleeve 1 by means of an outwardly bent tip of each anchoring element received within its respective slot 111-14 in sleeve 1, thereby preventing rotational movement of the nut with respect to the shaft 21 when the shaft is rotated, and constraining the movement of each anchoring member to a longitudinal movement.

FIGS. 3a and 3b illustrates modifications which may be provided for the same purpose. In FIG. 3a, each nut section 31a–34a is provided with a projection 31d–34d, respectively, received within a longitudinal groove 1a in the inner section of sleeve 1. In FIG. 3b, the bore in the sleeve 1 is of polygonal shape (e.g., square) as shown at 1a, whereupon the outer surface of the nuts 31c–34c would be of the shape so as to prevent the rotation of the nut upon the rotation of the shaft.

In order to extend the spikes through the slots, the shaft assembly 2 is rotated clockwise, causing nuts 31a and 32a to advance toward each other in a longitudinal direction. Cam member 24 positioned equidistantly between nuts 31a and 32a deflects spikes 31b, 31c, 32c and 32c radially outwardly through their respective slots as they move longitudinally as nuts 31a and 32a approach one another. Such clockwise rotation of shaft assembly 2 simultaneously causes nuts 33a and 34a to advance toward each other in a longitudinal direction. Cam member 25 positioned equidistantly between nuts 33a and 34a deflects spikes 33b, 33c, 34b and 34c radially outwardly through their respective slots as they move longitudinally as nuts 33a and 34a approach one another.

Continued rotation of the shaft causes the spikes to continue to extend through the slots until they reach and securely engage the osseous wall of the medullary canal. The degree of resistance to rotation provides a clear tactile signal to the surgeon that the spikes have engaged the osseous wall.

When the shaft assembly 2 is rotated counterclockwise, nuts 31a and 32a draw away from each other thereby disengaging spikes 31b, 31c, 32b and 32c from the bone and retracting them into the sleeve 1. Such counterclockwise rotation of shaft assembly 2 simultaneously causes nuts 33a and 34a draw away from each other thereby disengaging spikes 33b, 33c, 34b and 34c from the bone and retracting them into the sleeve 1. Upon retraction, all of the spikes return to their inoperative position within the sleeve, leaving a smooth and unobstructed surface for easy withdrawal of the device from the bone. If desired, the threads of the two ends of the shaft may have different pitches such that the rotation of the shaft produces different displacements of the nuts, and thereby of their respective anchoring elements 31–34, at the opposite ends of the shaft.

Many further embodiments of the invention may be made. For example, the device may be configured to have anchoring elements at either end or at both of its ends, as indicated by the injury to the bone. Moreover, the device may be of a length as indicated by the bone in question. To adjust the length of the device, a sleeve 1 of appropriate length is selected. The shaft assembly 2 is adaptable to the length of the sleeve by means of the coupling member 23 centrally disposed thereon. The central portion of the coupling member 23c may vary in length. A coupling member of the proper length is selected in order to configure a shaft assembly 2 of appropriate length to the sleeve 1.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

The foregoing disclosure and the showings made in the drawings are therefore to be considered as merely illustrative of the principles of the present invention and are not to be interpreted in a limiting sense since many other variations and applications of the invention may be made.

What is claimed is:

1. An internal fixation device particularly useful for securing bone fragments, comprising:
   a. an elongate tubular sleeve for insertion into the medullary canal of the bone fragments to be secured, said sleeve being formed with at least two slots therethrough at one end of the sleeve;
   b. an elongate shaft movable within said sleeve; and
   c. at least two anchoring elements, each having an inner end coupled to said shaft and an outer end aligned with one of said slots and displaceable radially outwardly therethrough to engage a bone fragment upon the movement of the shaft within the sleeve;
   d. the anchoring elements being oriented with respect to the shaft such that the outward displacement of one anchoring element moves its outer end to an oblique position facing one end of the shaft to anchor the engaged bone fragment against movement in one longitudinal direction, and the outward displacement of the other anchoring element moves its outer end to an oblique position facing the opposite end of the shaft to anchor the engaged bone fragment against movement in the opposite longitudinal direction.

2. The device according to claim 1, wherein said elongate shaft includes a pair of oppositely inclined cam surfaces at one end of the shaft and engageable with said two anchoring elements such that the movement of the shaft in one direction with respect to said sleeve displaces said anchoring elements radially outwardly to engage said bone fragment against movement in said opposite longitudinal directions.

3. The device according to claim 1, wherein there are at least two of said slots at each end of the sleeve, and wherein there are at least two of said anchoring elements at each end of the shaft outwardly displaceable through said slots.

4. The device according to claim 1, wherein each of said anchoring elements is of an elastic material permitting its outer end to be outwardly displaced by elastic deformation.

5. The device according to claim 1, wherein there are two pairs of said slots in said sleeve, and two pairs of said anchoring elements coupled at their inner ends to said shaft;
   one pair of anchoring elements being oriented such that their outer ends are outwardly displaceable through one pair of slots to engage a bone fragment and to anchor it against movement in one longitudinal direction;
   the other pair of anchoring elements being oriented such that their outer ends are outwardly displaceable through the other pair of slots to engage a bone fragment and to anchor it against movement in the opposite longitudinal direction.

6. The device according to claim 5, wherein there are two pairs of said slots and two pairs of said anchoring elements at each of the two opposite ends of said sleeve and shaft, respectively.

7. The device according to claim 1, wherein said shaft is rotatably movable within said sleeve, and the inner ends of said anchoring elements are coupled to said shaft to outwardly displace the outer ends of the anchoring elements upon rotation of the shaft within the sleeve.

8. The device according to claim 7, wherein said shaft is threaded, and the inner ends of said two anchoring elements are secured to two nuts threaded on said shaft and longitudinally movable with respect thereto upon the rotation of the shaft to outwardly displace the outer ends of the respective anchoring elements through their respective slots into engagement with said bone fragment.

9. The device according to claim 8, wherein said device includes a cam surface engageable by the outer end of each of said anchoring elements upon the longitudinal movement of the anchoring element, to outwardly displace the outer ends of the anchoring elements through their respective slots into engagement with said bone fragment.

10. The device according to claim 9, wherein each of said nuts is secured to the inner ends of at least two anchoring elements oriented in the same direction, the anchoring elements of one nut being oriented in the opposite direction with respect to the anchoring elements of the other nut such that the outward displacement of the outer ends of the anchoring element of one nut anchors the engaged bone fragment against movement in one longitudinal direction, and the outward displacement of the outer ends of the anchoring elements of the other nut anchors the engaged bone fragment against movement in the opposite longitudinal direction.

11. The device according to claim 10, wherein each nut is integrally formed with its respective anchoring elements.

12. The device according to claim 10, wherein said shaft is formed with a right hand thread receiving one of said nuts, and with a left hand thread receiving the other of said nuts, such that the rotation of the shaft in one direction moves said nuts and their respective anchoring elements in opposite longitudinal directions.

13. The device according to claim 12, wherein said cam surface is a cam member carried by said shaft between said right hand and left hand threads of the shaft, said cam member including a conical surface on each side engageable by the outer ends of the nut on the respective side, such that the rotation of the shaft in one direction causes the two nuts to move longitudinally towards the cam member to displace outwardly the outer ends of the anchoring elements of the two nuts, and the rotation of the shaft in the opposite direction causes the two nuts to move longitudinally away from the cam member to displace inwardly the outer ends of the anchoring elements of the two nuts.

14. The device according to claim 13, wherein the outer tips of said anchoring elements are bent outwardly to be received within their respective slots in the sleeve such as to prevent said nuts from moving circumferentially upon the rotation of said shaft.

15. The device according to claim 13, wherein said nuts have outer surfaces keyed to the inner surface of said sleeve such as to prevent the nuts from moving circumferentially upon the rotation of said shaft.

16. The device according to claim 14, wherein the outer surface of said nuts includes a projection received within a longitudinal recess in the inner surface of said sleeve preventing the nuts from moving circumferentially upon the rotation of said shaft.

17. The device according to claim 14, wherein the outer surfaces of said nuts and the inner surface of said sleeve are of a polygonal configuration preventing the nuts from moving circumferentially upon the rotation of said shaft.

18. The device according to claim 13, wherein each of the opposite ends of said shaft is formed with said right hand and left hand threads with a said cam member in between, and carries said two nuts such that the anchoring elements of the two nuts at each end of the shaft engage and anchor the opposite ends of the bone fragments to be secured.

19. The device according to claim 18, wherein said threads at the two ends of the shaft have different pitches, such that the rotation of the shaft produces different displacements of the nuts at the opposite ends of the shaft.

20. The device according to claim 12, wherein said shaft includes a first end section constituted of one of said opposite ends, a second end section constituted of the other of said opposite ends, and a coupling member joining said first and second end sections.

* * * * *